(12) United States Patent
Husebo et al.

(10) Patent No.: US 8,791,406 B2
(45) Date of Patent: Jul. 29, 2014

(54) METHOD AND APPARATUS FOR DETERMINING A FLUID DENSITY

(75) Inventors: Magne Kjetil Husebo, Tertnes (NO); Tor Magnus Saevareide, Bergen (NO)

(73) Assignee: Johnson Matthey, PLC, London (GB)

( * ) Notice: Subject to any disclaimer, the term of this patent is extended or adjusted under 35 U.S.C. 154(b) by 80 days.

(21) Appl. No.: 13/499,770

(22) PCT Filed: Sep. 28, 2010

(86) PCT No.: PCT/GB2010/051618
§ 371 (c)(1), (2), (4) Date: Jun. 25, 2012

(87) PCT Pub. No.: WO2011/039534
PCT Pub. Date: Apr. 7, 2011

(65) Prior Publication Data
US 2012/0256086 A1    Oct. 11, 2012

(30) Foreign Application Priority Data

Oct. 1, 2009 (GB) .................................. 0917216.4

(51) Int. Cl.
*G21K 5/00* (2006.01)
(52) U.S. Cl.
USPC ..................... 250/251; 250/336.1; 250/356.1; 250/357.1; 73/32 R; 73/37; 73/53.01; 73/61.68; 73/170.01; 73/170.14; 73/521
(58) Field of Classification Search
USPC ......... 250/251, 336.1, 356.1, 357.1; 73/32 R, 73/37, 53.01, 53.04, 61.68, 170.01, 73/170.14, 521
See application file for complete search history.

(56) References Cited

U.S. PATENT DOCUMENTS

| | | | |
|---|---|---|---|
| 2,857,522 A | 10/1958 | Jones | |
| 2,899,555 A | 8/1959 | Fries | |
| 3,766,379 A | 10/1973 | Parkinson | |
| 3,960,756 A * | 6/1976 | Noakes | ..................... 252/301.18 |
| 4,506,541 A | 3/1985 | Cunningham | |

(Continued)

FOREIGN PATENT DOCUMENTS

| | | |
|---|---|---|
| DE | 37 23 437 A1 | 6/1988 |
| FR | 2.080.134 | 11/1971 |
| WO | WO-87/07021 A1 | 11/1987 |
| WO | WO-2006/067525 A1 | 6/2006 |

OTHER PUBLICATIONS

International Search Report dated Dec. 22, 2010, from PCT International Application No. PCT/GB2010/051618.

(Continued)

*Primary Examiner* — Nicole Ippolito
(74) *Attorney, Agent, or Firm* — RatnerPrestia

(57) ABSTRACT

The invention provides an apparatus and method for measuring a property of a gas, such as the amount of liquid in a stream of the gas. The apparatus comprises a source of beta particles (20), a detector (23) capable of detecting beta particles, means (18) to support said source and said detector spaced apart from each other such that gas may enter the space between the source and detector and that the source is positioned to emit beta particles towards said detector; wherein said detector comprises a scintillation material in optical communication with a photodetector (26), and means (24) to physically isolate said photodetector from said gas.

21 Claims, 2 Drawing Sheets

(56) References Cited

U.S. PATENT DOCUMENTS

| | | | |
|---|---|---|---|
| 4,682,034 | A | 7/1987 | Saint et al. |
| 6,389,908 | B1 | 5/2002 | Chevalier et al. |
| 7,111,496 | B1 * | 9/2006 | Lilienfeld et al. ............ 73/28.01 |
| 2009/0114012 | A1 | 5/2009 | Becherer et al. |
| 2011/0198488 | A1 * | 8/2011 | Stoller et al. .................. 250/258 |

OTHER PUBLICATIONS

British Search Report dated Dec. 1, 2009, from British Patent Application No. 0917216.4.

International Preliminary Report on Patentability dated Apr. 3, 2012, from PCT International Application No. PCT/GB2010/051618.

* cited by examiner

US 8,791,406 B2

METHOD AND APPARATUS FOR DETERMINING A FLUID DENSITY

CROSS-REFERENCE TO RELATED APPLICATIONS

This application is the U.S. National Phase application of PCT International Application No. PCT/GB2010/051618, filed Sep. 28, 2010, and claims priority of British Patent Application No. 0917216.4, filed Oct. 1, 2009, the disclosures of both of which are incorporated herein by reference in their entireties for all purposes.

FIELD OF THE INVENTION

The present invention concerns an instrument suitable for detecting a liquid entrained in a gas, particularly a flowing gas stream such as a hydrocarbon gas stream.

BACKGROUND OF THE INVENTION

Natural gas recovered from underground reservoirs is usually compressed and cooled prior to storage and transport to the point of sale or use. Liquid is often found in natural gas streams and it is important to remove as much water or condensed hydrocarbons from the gas as possible in order to avoid damage to compressors and other process equipment. Liquid components are removed from natural gas streams by various means, for example using gas scrubbers and other forms of separator. It is desirable to measure the amount of liquid remaining in a gas stream after it has been treated in order to ensure as complete removal as possible.

The use of nucleonic gauges is common for measuring the bulk density of a process fluid for determining level or a density profile of a multiphase fluid for example. Such gauges typically measure the gamma radiation that passes through the fluid and which is detected by a detector. Gauges based on the transmission of gamma radiation are not, however, sufficiently sensitive to detect small changes in the density of a gas. The detection of small amounts of liquid entrained in a gas stream is of commercial importance in the gas supply industry for the reasons already discussed and yet the resulting changes in the gas density are typically too small for the existing gamma gauges to detect. WO06/067525 describes a method of detecting liquid in a gas stream by measuring changes in the bulk density of a gas stream using gamma radiation. The radiation source and detector are located outside a vessel such as a high-pressure gas pipeline and radiation passes from the source through the pipe to the detector. The radiation enters and exits the pipe walls through titanium dip tubes which are much less attenuating to the radiation than the material of the pipe walls. U.S. Pat. No. 6,389,908 describes an alternative method using gamma radiation, where the gamma is transmitted through a narrowed portion of a pipeline through beryllium windows inserted into the pipe walls. In order to increase the sensitivity of such a method, it is necessary to use less energetic radiation such as X-rays or beta particles. Beta gauges are currently used for measuring online the thickness of paper in paper mills. However, beta particles are of such low energies that they are unable to penetrate the dip tubes or beryllium windows used in the prior gauges. It is an object of the invention to provide a method for determining the bulk density of a gas stream which is suitable for estimating the amount of a liquid present in order to monitor the effectiveness of liquid removal processes.

SUMMARY OF THE INVENTION

According to the invention, we provide a method for measuring a property of a fluid comprising:
(a) providing a source of beta particles and a detector for detecting said beta particles, wherein said source and detector are spaced apart from one another and in contact with the fluid; and wherein said source and detector are arranged such that beta particles emitted by said source are capable of being detected by said detector
(b) causing at least a part of said fluid to flow between said source and said detector;
(c) measuring over a time period the number of beta particles detected by said detector and inferring a change in said property from a change in the number of beta particles detected over said time period.

According to the invention, we provide an apparatus, suitable for measuring a property of a fluid, comprising a source of beta particles, a detector capable of detecting beta particles, means to support said source and said detector spaced apart from each other and in contact with the fluid, such that fluid may enter the space between the source and detector and that the source is positioned to emit beta particles towards said detector; wherein said detector comprises a scintillation material in optical communication with a photodetector, and means to physically isolate said photodetector from said fluid.

BRIEF DESCRIPTION OF THE DRAWINGS

Preferred embodiments of the invention will be further described with reference to the drawings, which are:—

DETAILED DESCRIPTION OF THE INVENTION

Figure 1:
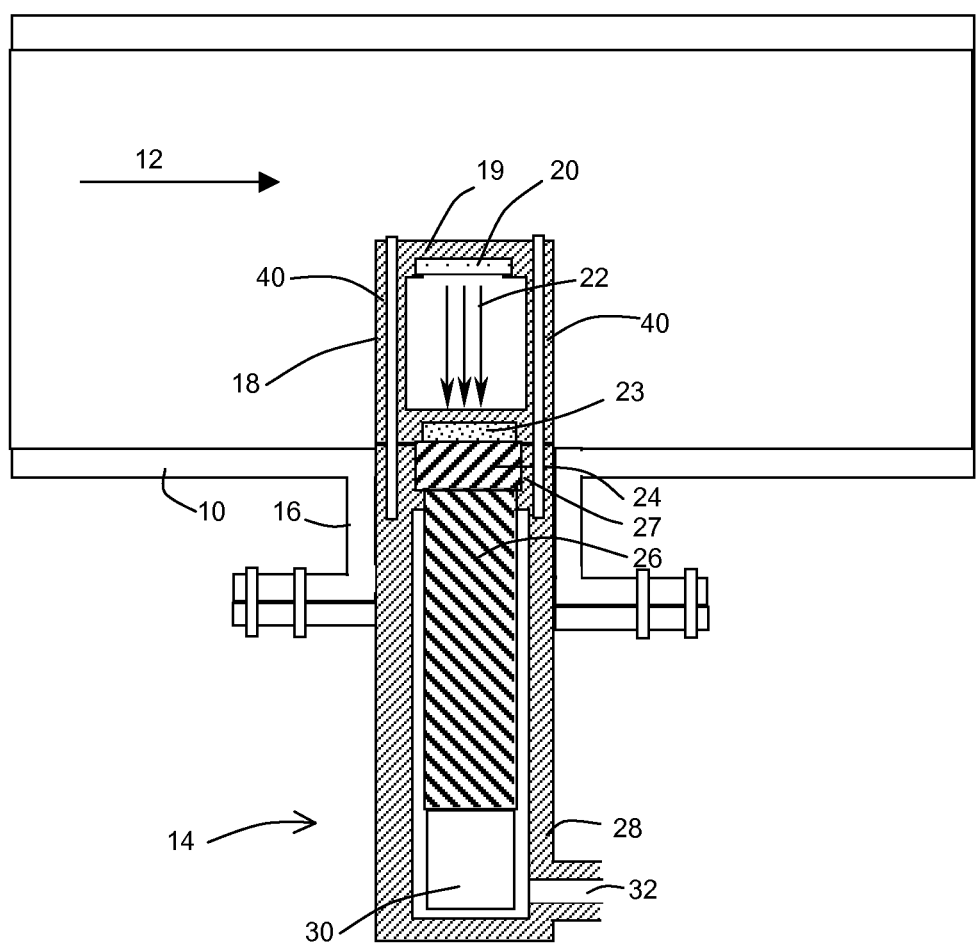
FIG. 1, a sectional schematic view through one embodiment of the density gauge of the invention.

In a preferred method, the property measured is the bulk density of said fluid. The fluid preferably comprises a gas-containing stream. The presence of liquid in the gas-containing stream may be detected as an increase in the bulk density of the stream. When the density of the gas stream increases, beta particles are absorbed by the gas stream so that fewer beta particles are detected by the detector. The resulting attenuation of the beta particles can be related directly to the change in bulk density of the fluid. An absolute value of density can also be calculated based on a suitable calibration, if required. The measured property may alternatively be a fluid pressure or composition or changes therein which can be derived from a measurement of or changes in the bulk density of the fluid.

Beta gauges have not hitherto been used for measuring (changes in) the density of a hydrocarbon gas stream because when the gas stream forms a potentially explosive mixture, it is necessary to avoid introducing any source of ignition into the gas stream. Nucleonic density gauges require electronic systems, associated with the detector or data processing and control functions, and therefore are unsuitable for introducing into a gas flow when the gas is potentially explosive. It is therefore a further object of the invention to provide an apparatus suitable for measuring the bulk density of a flowing hydrocarbon gas.

The apparatus of the invention therefore enables low-energy beta particles to be used for measuring a property, such as the bulk density, of fluid such as a flowing gas stream in a pipeline whilst overcoming the problem that beta particles cannot penetrate through metal pipeline walls. Using the apparatus of the invention for this purpose maintains the necessary separation between the electronic parts of the gauge and a flowing gas stream by placing the source and detector in the gas flow, and the photodetector and other electronic parts of the gauge outside the pipeline. In this way only the light emitted by the detector is required to pass through the walls of the pipeline. The apparatus is sensitive to changes in the bulk density of the gas, caused for example by changes in composition or pressure, because the bulk density of the gas affects the number of beta particles emitted by the source which are detected by the detector. The apparatus may therefore be referred to as a density gauge.

The photodetector comprises a photomultiplier tube or photodiode. A photomultiplier tube is a preferred photodetector. Photomultipliers typically require high voltage (typically about 1000V) for their operation and the voltage generator and associated electronics represents a potential source of ignition which is not suitable for installation within a vessel containing explosive gas. In the apparatus of the invention, the photodetector and associated electronic apparatus is physically isolated from the fluid which is to be measured using the density gauge. This feature allows the density gauge to be used to measure the bulk density (and thus provide an estimate of the liquid content of) hydrocarbon gases flowing through a pipeline. The means of isolation typically comprises placing the photodetector and electronic apparatus in a location which is separated from the gas by a gas-proof and preferably pressure-resistant seal, comprising for example a gasket. The photodetector may be placed in an enclosure, said enclosure being adapted to exclude the ingress of the gas being measured.

The photodetector is in optical communication with the scintillation detector, whilst being physically isolated from the fluid. In a preferred embodiment this is achieved by means of a window of material which transmits light from the scintillation detector to the photomultiplier. Preferred materials are sufficiently durable and resistant to abrasion to be deployed in a high pressure gas flow, and include glasses of appropriate optical clarity to transmit the light generated by the scintillator. Sapphire glass is a preferred material. The window forms a physical barrier between the gas flow which is measured by the density gauge and the photomultiplier and any associated electronic apparatus. The window is typically incorporated into a casing or housing which is typically formed of a suitable material such as a steel. The interface between the housing material and the window is sealed using known methods of forming a fluid-proof and preferably pressure-proof seal. The scintillator and photodetector are optically coupled to the window material so that light generated by the scintillator (in contact with the gas to be measured) passes through the window into the photodetector which is sealed by the window material away from contact with the fluid being measured.

More than one separate window of optically conducting material may be provided between said photodetector and said fluid. The use of more than one window may be preferred in order to provide a suitable environment in which the photodetector is located which has a sufficiently low risk of containing explosive gas of explosive gases so that the instrument may be approved for use in hazardous locations. The additional physical barrier of one or more additional windows may provide that the detector is in an electrical safety zone 1 instead of a zone 0. Zone 0 is where explosive gas is always present and zone 1 only has the possibility of explosive gas being present according to standard hazardous working regulations. The use of more than one window between the scintillator and the photodetector may enable the instrument to achieve electrical safety certification as an explosion proof design.

The source of beta particles is selected from known commercially available beta sources, for example strontium-90. Commercial sources typically comprise the emitting element encased in a second material. A strontium source encapsulated in stainless steel or nickel is suitable for use in the present invention, being mechanically robust and also resistant to corrosion; alternative sources and capsules may be selected as appropriate.

The detector is a scintillation detector, which may be a scintillation crystal or a plastics scintillation material. A scintillation crystal is preferred. Many useful scintillation crystals are known, including alkali metal halides, such as NaI, which may be doped with an activator. Examples include NaI(Tl) (sodium iodide doped with thallium), CsI(Tl), CsI(Na), CsI (pure), CsF, KI(Tl), LiI(Eu). Non-alkali crystals include: $BaF_2$, $CaF_2(Eu)$, ZnS(Ag), $CaWO_4$, $CdWO_4$, YAG crystals, such as YAG(Ce) ($Y_3Al_5O_{12}(Ce)$); GSO (gadolinium oxyorthosilicate), LSO ($Lu_2SiO_5$), LYSO ($Lu_{1.8}Y_{0.2}SiO_5(Ce)$), BGO (bismuth germanate), lanthanum halides. The appropriate scintillator may be selected by the skilled person, based upon its physical and chemical properties (hardness, density, hygroscopicity etc) and scintillation properties such as light output and decay time. We have found that a YAG crystal is a suitable detector when the density gauge is to be used for detecting density changes due to small amounts of liquid entrained in a hydrocarbon gas stream.

The beta source and the detector are spaced apart from each other, preferably by a known predetermined distance, such that the fluid to be measured may enter the space between the source and detector and that the source is positioned to emit beta particles towards said detector. This is achieved by mounting the source and detector on a support in the required orientation. The source and detector supports are preferably joined to form a unitary support. The distance between the source and detector depends on the energy of the source, the range of density of the material to be measured and the space available for operating the density gauge. For a strontium-90 source used for measuring the density changes due to small amounts of liquid entrained in a hydrocarbon gas stream, the distance between the source and detector may conveniently fall in the range 2-20 cm, especially about 10 cm. The support is preferably sufficiently robust for use in a gas at high pressure and preferably capable of operating in high velocity gas flows without affecting the measurement of density and without deforming, eroding or corroding to an extent that would affect the accuracy of the measurements.

The photodetector is coupled to a means of counting and recording the scintillation events including a signal processor and data processing module. The signal and data processing includes appropriate smoothing and averaging algorithms for minimizing data error whilst detecting changes in the signal with appropriate sensitivity. Suitable signal and data handling procedures are known within the art of nucleonic gauges and will not be further described. Signal and data handling may be carried out in the proximity of the photodetector or in a remote location. Means for transmitting a signal from the photomultiplier or from a signal and/or data processing module are provided and include cables and also wireless transmission means. A power supply is provided for the photodetector and other electrical equipment.

The method of the invention is preferably carried out using a density gauge according to the invention. Changes in a physical or chemical property of the fluid may be calculated from the difference between the number of beta particles detected by the detector over a period of time. The number of beta particles emitted by the source that are detected by the detector is proportional to the bulk density of the fluid in the path of the beta particles between the source and the detector. The number of detected beta particles may be used to calculate an absolute value of bulk density, or a derived property, based on calibration. Alternatively, the number of beta particles detected may be monitored over time intervals to detect significant changes in the detected beta particles within a period of time, and the information used to infer a change in the fluid. An important application for the method is the detection of small amounts of liquid such as water and condensed hydrocarbons entrained in a hydrocarbon gas stream exiting process equipment such as gas scrubbers used in the treatment of natural gas produced from oil & gas reservoirs. We have found that it is possible to detect less than 0.01% by volume of liquid in such a gas stream and that the density gauge may be capable of detecting as little as 0.002% by volume of liquid in the gas stream. For a single gauge, the bulk density of the fluid between source and scintillator depends on the density of the dry gas (which depends on its temperature, pressure and gas composition i.e. molecular weight); and the density of entrained liquid and the liquid content (vol %). So, in order to calculate the amount of liquid in the pipe, it is necessary to take account of the pipeline pressure, temperature and dry gas molecular weight. Corrections for changes in pressure/temperature and molecular weight may be made in the proximity of the photomultiplier or in a remote location. If the gas is known to be dry (zero liquid content), the measured bulk density depends on pressure, temperature and gas molecular weight. So, for dry gas, when temperature and pressure are known, it is possible to calculate the molecular weight of the gas, which may be useful in several applications in the process industries. Alternatively, if the gas is known to be dry and its molecular weight and the pipeline temperature is known, the density (or the attenuation of beta particles) measured by the gauge may be used to calculate the pipeline pressure. We have found that the gauge of the invention is very sensitive to pressure enabling resolution of pressure changes of a few millibars.

In use, the source, detector and support are installed in contact with the fluid to be monitored. In a preferred embodiment the source, detector and support are installed within the lumen of a pipeline carrying a flow of gas and/or liquid, in such a way that gas can flow between the source and detector. The interior of the pipeline is sealed from an enclosure containing the photodetector and associated electrical equipment. The barrier between the interior of the pipeline and the enclosure comprises, in part, a window of a material that is transparent to the radiation produced by the scintillation detector.

In a preferred embodiment of the method of the invention, a first source and first detector are provided at a first location in the fluid and a reference source and reference detector are provided at a second location in contact with a fluid and said property is calculated from the difference between the number of beta particles detected by the first detector and the number of beta particles detected by the reference detector. In this embodiment more than one density gauge according to the invention may be used to determine the bulk density of fluid, such as a gas, flowing in a pipeline. When a first density gauge is installed within a gas stream flowing in the pipeline, a second density gauge may be installed as a reference gauge in a location where the gas composition is not subject to change whilst the temperature and pressure are substantially the same as those experienced within the main pipeline. Such a location may include a branch of pipeline in communication with the main pipeline, optionally separated from the main pipeline by a de-mister. In operation, the density or a measured parameter related to the density, such as radiation counts measured by the detector, as recorded at each of the density gauges, is compared and differences between the measured densities are attributed to a change in the bulk density measured in the main pipeline. Changes in a physical or chemical property of the fluid may be calculated from the difference between the number of beta particles detected by the first detector and the beta particles detected by the reference detector. In this way changes in the transmission or detection of beta particles due to temperature, pressure or source decay may be accommodated, provided care is taken to ensure that each density gauge experiences substantially the same environmental conditions. Preferably the reference gauge is substantially functionally identical to the first density gauge. By substantially functionally identical we mean that the parameters of the density gauges which affect response to changes in density of a gas between the source and detector, including, the dimensions, source and detector type, source activity etc, are substantially identical. More than two density gauges may be employed and monitored.

The drawing shows a pipeline 10 through which gas flows in a direction shown by arrow 12. A density gauge 14 according to the invention is inserted through a flanged port 16 into the path of gas flow. The density gauge comprises a support 18 for supporting a $^{90}$Sr—containing source of beta particles 20 which are emitted in the direction of the arrows 22 towards a scintillation detector 23 comprising a YAG crystal. A housing 28 contains a photomultiplier 26 and a high-voltage generator 30 in addition to cabling for carrying signals generated by the photomultiplier to a control and data processing unit (not shown) via port 32. A sapphire glass window 24 forms a pressure resistant seal by means of a gasket 27 with the housing 28. The scintillator 23 is optically coupled to the sapphire window 24, which is optically coupled to the photomultiplier 26 so that, in operation, light emitted by the scintillator passes through the window 24 to the photomultiplier.

Figure 2:
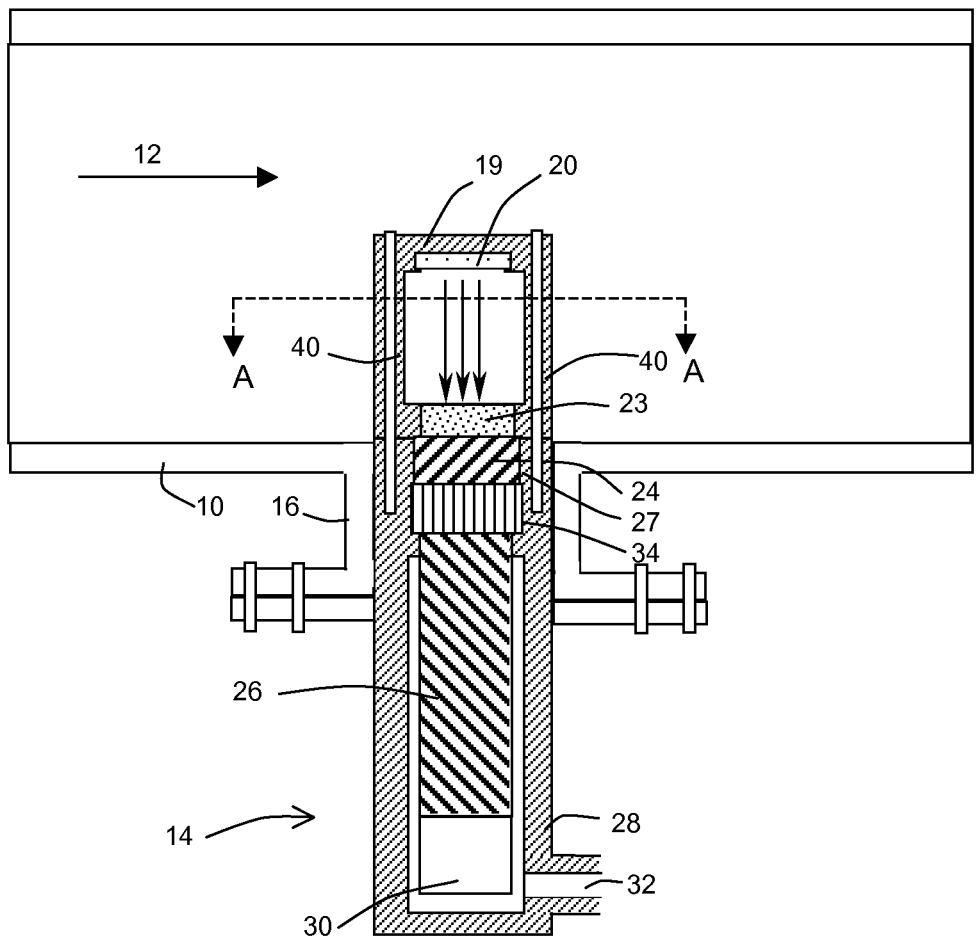
FIG. 2, a sectional schematic view through a second embodiment of the density gauge of the invention.

A second embodiment of the invention is shown in FIG. 2, in which an additional window 34 is placed between the scintillator and the detector. This additional gas-resistant barrier is provided to ensure that the detector is in an electrical safety zone 1 in order that the instrument may achieve electrical safety certification for an explosion proof design. The skilled person will understand that in the field of certification of electrical equipment for use in hazardous areas, zone 0 is where explosive gas is always present and zone 1 only has the possibility of explosive gas being present.

Figure 3:
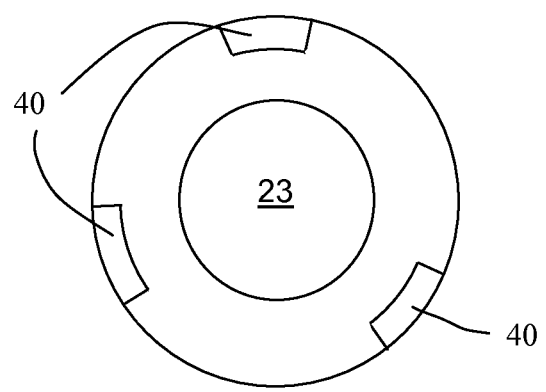
FIG. 3, a cross-sectional schematic view through line A-A of FIG. 2.

FIG. 3 shows a cross-section through the density gauge along lines A-A of FIG. 2. This shows that the support 18 has three struts 40 which support the source housing 19. In use, the fluid to be measured can flow between the source 20 and the detector 23 through adjacent struts 40.

The invention claimed is:

1. An apparatus, suitable for measuring a property of a fluid, comprising a source of beta particles, a detector capable of detecting beta particles, means to support said source and said detector spaced apart from each other and in contact with said fluid, such that fluid may enter the space between the source and detector and that the source is positioned to emit beta particles towards said detector; wherein said detector comprises a scintillation material in optical communication with a photodetector, and means to physically isolate said photodetector from said fluid.

2. An apparatus according to claim 1, wherein the photodetector is located within an enclosure, said enclosure being adapted to exclude the ingress of the fluid being measured.

3. An apparatus according to claim 1 wherein said photodetector is separated from the fluid by a fluid-proof seal.

4. An apparatus according to claim 1, wherein said means to physically isolate said photodetector from said fluid comprises a window of optically conducting material placed between said scintillation material and said photodetector, said optically conducting material being capable of transmitting light from the scintillation detector to the photodetector.

5. An apparatus according to claim 4, wherein more than one separate window of optically conducting material is provided between said photodetector and said fluid.

6. An apparatus according to claim 4, wherein said scintillation material and said photodetector are optically coupled to said optically conducting material, said optically coupled material being disposed between said scintillation material and said photodetector.

7. An apparatus according to claim 1, wherein said scintillation material comprises a scintillation crystal.

8. A method of measuring changes in a physical or chemical property of a hydrocarbon-containing fluid stream using an apparatus according to claim 1, comprising the steps of installing the apparatus such that said source and detector are within a vessel containing said hydrocarbon fluid and said photodetector is outside said vessel, causing said fluid to flow between the source and detector and calculating changes in the physical or chemical property of the fluid stream from measured changes in the number of beta particles emitted by the source which are detected by the detector.

9. A method according to claim 8, wherein said property is the bulk density of said fluid.

10. A method according to claim 8, wherein said fluid comprises a gas and the method detects the presence of liquid in said gas.

11. A method according to claim 8, wherein a first source and first detector are provided at a first location in contact with the fluid and a reference source and reference detector are provided at a second location in contact with a fluid and said property is calculated from the difference between the beta particles detected by the first detector and the beta particles detected by the reference detector.

12. A method according to claim 11, wherein the reference source and detector are substantially functionally identical to the first source and detector.

13. A method according to claim 11, wherein said first location is within a gas stream flowing in a pipeline and the temperature and pressure at said second location are substantially the same as those experienced at said first location.

14. A method according to claim 13, wherein said second location is in communication with said first location and separated therefrom by a de-mister.

15. A method for measuring a property of a fluid comprising:
   (a) providing a source of beta particles and a detector for detecting said beta particles, wherein said source and detector are spaced apart from one another and in contact with said fluid; wherein said source and detector are arranged such that beta particles emitted by said source are capable of being detected by said detector; and wherein said detector comprises a scintillation material in optical communication with a photodetector, and means to physically isolate said photodetector from said fluid;
   (b) causing at least a part of said fluid to flow between said source and said detector; and
   (c) measuring over a time period the number of beta particles detected by said detector and inferring a change in said property from a change in the number of beta particles detected over said time period.

16. A method according to claim 15, wherein said property is the bulk density of said fluid.

17. A method according to claim 15, for measuring the composition of said fluid.

18. A method according to claim 17, wherein said fluid comprises a gas and the method detects the presence of liquid in said gas.

19. A method according to claim 15, for measuring the pressure of said fluid.

20. A method according to claim 15, wherein a first source and first detector are provided at a first location in contact with the fluid and a reference source and reference detector are provided at a second location in contact with a fluid and said property is calculated from the difference between the beta particles detected by the first detector and the beta particles detected by the reference detector.

21. A method according to claim 20, wherein the reference source and detector are substantially functionally identical to the first source and detector.

* * * * *